United States Patent
Streicher

(10) Patent No.: US 6,656,737 B1
(45) Date of Patent: Dec. 2, 2003

(54) ISOCYNATE DERIVATIZING AGENT AND METHODS OF PRODUCTION AND USE

(75) Inventor: Robert P. Streicher, Cincinnati, OH (US)

(73) Assignee: The United States of America as represented by the Department of Health and Human Services, Washington, DC (US)

(*) Notice: Subject to any disclaimer, the term of this patent is extended or adjusted under 35 U.S.C. 154(b) by 0 days.

(21) Appl. No.: 09/700,155
(22) PCT Filed: May 13, 1999
(86) PCT No.: PCT/US99/10634
§ 371 (c)(1), (2), (4) Date: Jan. 23, 2001
(87) PCT Pub. No.: WO99/58517
PCT Pub. Date: Nov. 18, 1999

(51) Int. Cl.[7] .................. G01N 33/00; C07C 403/00; C07C 275/00; C07C 211/00
(52) U.S. Cl. .................. 436/106; 585/400; 564/32; 564/47; 564/305; 564/315; 562/405; 562/433; 562/442; 560/8; 560/19; 560/20; 560/21
(58) Field of Search .................. 436/106; 585/400; 564/32, 47, 305, 315; 562/405, 433, 442; 560/8, 19, 20, 21

(56) References Cited

U.S. PATENT DOCUMENTS 5,354,689 A    10/1994  Streicher
5,414,069 A  *  5/1995  Cumming et al. .......... 528/310

OTHER PUBLICATIONS

Wade et al. "Benzenesul fonylcarbonitrile Oxide.5. Face Selectivity of Cycloaddition to Chiral Terminal Alkenes" *Tetrahedron* 40(3):601–611 (1984).

* cited by examiner

*Primary Examiner*—Jill Warden
*Assistant Examiner*—Monique T. Cole
(74) *Attorney, Agent, or Firm*—Needle & Rosenberg P.C.

(57) ABSTRACT

An organic compound useful for detecting the total quantity of isocyanate in an environmental sample is provided. The compound is 9-anthrcenylmethyl-1-piperazinecarboxylate (PAC), an isocyanate derivatizing agent. A process for producing PAC and methods for detecting a particular isocyanate monomer or the total isocyanate in environmental samples using PAC & related isocyanate derivatizing agents are also provided.

24 Claims, 2 Drawing Sheets

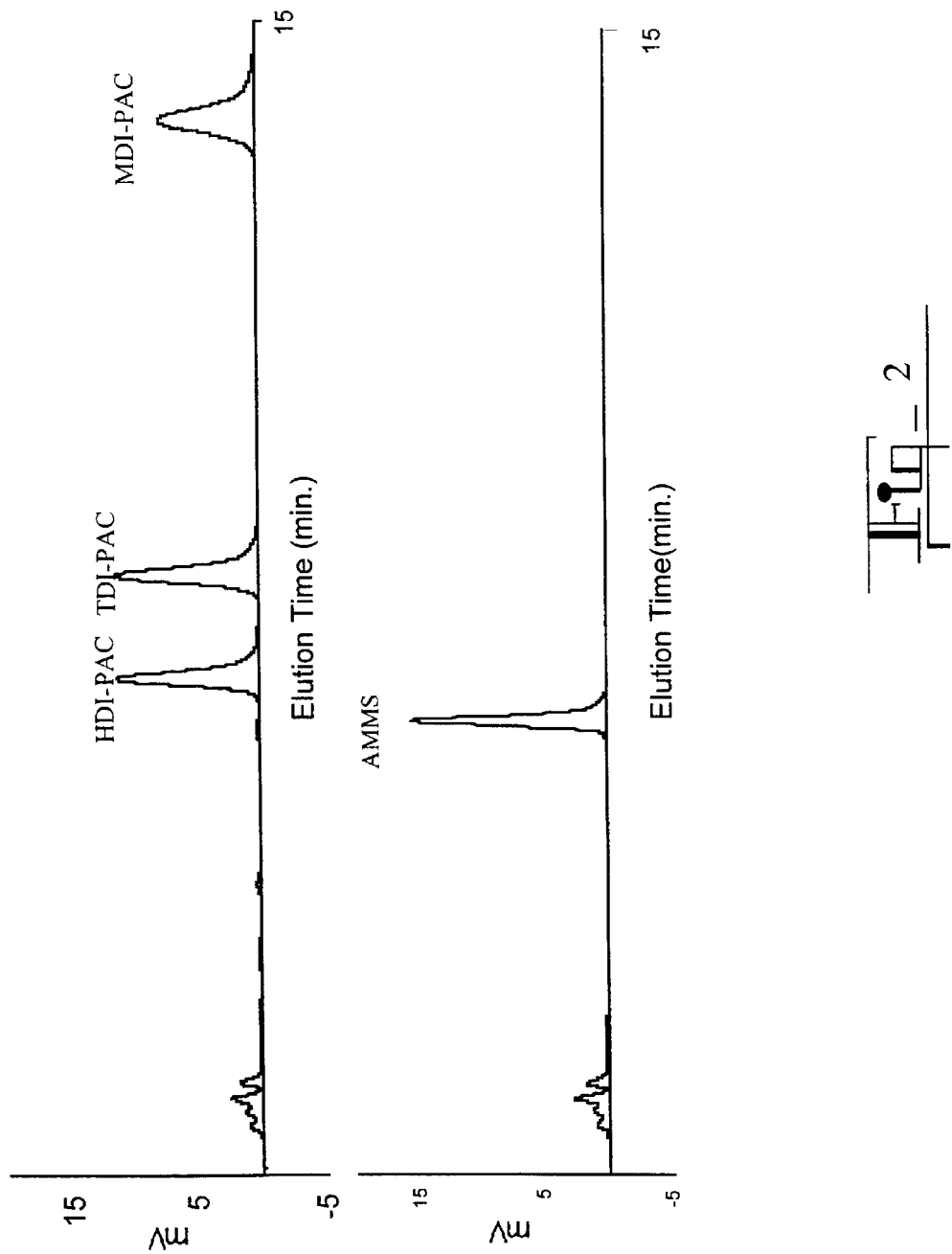
FIG_2

ISOCYNATE DERIVATIZING AGENT AND METHODS OF PRODUCTION AND USE

This invention was made in the Centers for Disease Control and Prevention, an agency of the United States Government. The U.S. Government has certain rights in this invention.

FIELD OF THE INVENTION

The present invention relates generally to the fields of organic and analytical chemistry and more particularly to a denivatizing agent and method for detecting and quantifying isocyanate contamination in a sample, such as an environmental sample.

BACKGROUND OF THE INVENTION

Isocyanates are a class of organic compounds, containing the isocyanate functional group —N=C=O. Isocyanates are used in the production of a wide variety of products, such as herbicides, crop protecting agents, antidiabetic agents, and polyurethane materials, including foams for insulation, seating, and paints with durable finishes. The most common isocyanates employed in industry are 2,4- and 2,6-toluene diisocyanate (TDI), 4,4'-diphenylmethane diisocyanate (MDI), hexamethylene diisocyanate (HDI), and isophorone diisocyanate (IPDI).

Although isocyanates are commercially beneficial, they have been known to create significant health risks. For example, isocyanates are severe respiratory irritants and can cause irritation of the eyes and mucous membranes. Prolonged exposure may result in permanent respiratory impairment. Because of the serious health risks associated with the use of isocyanates by industrial workers, most industrialized countries have set limits on the permissible levels of exposure. For example, the National Institute for Occupational Safety and Health (NIOSH) in the United States has set a level of 5 ppb; the Deutsche Forschungsgemeinschaft in the Federal Republic of Germany has set a limit of 10 ppb; and the Health and Safety Executive of the United Kingdom has created a standard of 20 $\mu$g NCO m$^{-3}$ for an eight hour time-weighted average and 70 $\mu$g NCO m$^{-3}$ for a ten minute time-weighted average.

In many environments, the hazard posed by isocyanate contamination in the air is not limited to a single isocyanate species. Products made using isocyanates may contain several different isocyanate species and new species may be released during use of the product. Therefore, it is important to assess the total hazard resulting from exposure to isocyanates, which requires measuring all isocyanate species. However, analytical standards are unavailable for a majority of these species, preventing individual identification of all isocyanate species in routine sample analysis.

A number of methods for measuring isocyanate monomers have been developed. Many of these are reviewed by Pumnell, el al. (*Analyst*, 110:893–905, 1985) and Dharmarajan, et al. (*Sampling & Calibration for Atmospheric Measurements*: 190–202, 1987). Almost all of these analytical methods are based upon the measurement of certain individual isocyanate species and, therefore, cannot measure total isocyanate concentration.

Marcali (*Anal. Chem.*, 29(4): 552–58, 1957) describes a calorimetric method for the measurement of isocyanate monomer. The Marcali method is limited to the measurement of aromatic isocyanates. Furthermore, the Marcali method is susceptible to interferences, exhibits poor sensitivity when compared with standard chromatographic methods, and the response varies with isocyanate structure.

Another method currently used to measure isocyanates is Method 25 for the Determination of Hazardous Substances (MDHS 25) of the Health Safety Executive of the United Kingdom. This method employs 1-(2-methoxyphenyl)-piperazine (MOPP) to derivatize isocyanate species. The derivatives are then analyzed with high performance liquid chromatography (HPLC) using ultraviolet and electrochemical detectors in series (HPLCJUV/EC). (*Health and Safety Executive: Occupational Medicine aid Hygiene Laboratory*, March 1987). Bagon, et al. (*Am. Ind. Hyg. Assoc. J.*, 45(1):39–43, 1984) disclose the use of MDHS 25 for determining isocyanate monomers and prepolymer relative to a monomer standard. The MDHS 25 method has been found to be unreliable in its ability to correctly identify isocyanate species and inaccurate in its quantitation of those species. (Streicher, et al., *Am. Ind. Hyg. Assoc. J.*, 56: 437–42, 1995).

A similar method has been developed by Wu, et al. (*Analyst*, 116(1): 21–5, 1991), in which tryptamine is employed as a derivatizing reagent followed by detection of the derivative using HPLC with fluorescence and electrochemical detectors in series. Although the Wu, et al. method appears to give more selective detection with less response factor variability than the IMDHS 25 method, all compounds must elute as observable peaks, and the analysis assumes that all isocyanates derived from a particular monomer have the same detector response factor. However, it has been found that the detector response factors of several tryptamine-derivatized isocyanates vary significantly. This method also requires the use of two detectors to confirm the identity of peaks as derivatized isocyanates.

U.S. Pat. No. 3,533,750 to Belisle discloses a process for detecting toluene diisocyanate, other aromatic isocyanates, or aromatic amines in ambient air. The method involves contacting an air sample with an acid solution of glutaconic aldehyde and then with a cationic ion exchange resin. The isocyanate is converted to a corresponding amine that is reacted with a reagent to produce a yellow color that is concentrated on the surface of the resin. Although the method is quick and sensitive, it cannot be used to detect aliphatic isocyanate species.

Schmidtke, et al. (*Fresenius J. Anal. Chem.*, 336(8): 647–54, 1990) teach a sensitive high performance liquid chromatographic procedure to analyze hexamethylene diisocyanate (HDI), 2,4- and 2,6-toluene diisocyanate (TDI) and 4,4'-diphenylmethane diisocyanate (MDI) in air. The isocyanates are trapped on a sorbent coated with 1-(2-methoxyphenyl)piperazine (MOPP). The resulting derivatives are separated using a column switching technique employing either a diode array UV detector or an electrochemical detector.

Hanus, et al. (*Mikrochimica Acta*, 3(1/6): 197–206, 1988) disclose the use of tubes packed with Chromosorb WAW, end-plugged with glass wool and impregnated throughout with 1-(2-pyridyl)piperazine for collection and in situ derivatization of toluene 2,4-diisocyanate (TDI), 4,4'-diphenylmethane diisocyanate (MDI) and 1,6-hexamethylene diisocyanate (HDI), which are collected from air. The compounds are desorbed and detected by ion-pair chromatography using a LiChrosorb RP-18 column.

Dalene, et al. (*J. Chromat.*, 435: 469–81, 1988) disclose a high performance liquid chromatographic method for the trace analysis of complex air mixtures containing 2,6- and 2,4-toluene diisocyanates and related amino isocyanates and diamines. The method is based on derivatization of the isocyanate functional groups to corresponding urethane groups with alkaline ethanol as the sampling and reacting medium.

Wu, et al. (*Am. Ind. Hyg. Assoc. J.*, 47(8): 482–87, 1986) describe a procedure for detecting isophorone diisocyanate (1-isocyanato-3-isocyanatomethyl-3,5,5-trimethylcyclohexane) by drawing air through a solution containing one of the following derivatizing agents: 1-(2-methoxyphenyl) piperazine, N-(4-nitrobenzyl)propylarine, or dibenzylamine. The reaction forms the corresponding urea derivatives which are then determined by HPLC using a LiChrosorb RP-18 column. Although relative recoveries are good (97–104%), the stability of the isophorone diisocyanate solution is low, having a half-life of approximately 3.8 days in acetonitrile.

The determination of isocyanates in air by nornal-phase liquid chromatography with fluorescence detection is described by Kormos, et al. (*Anal. Cheni.*, 53(7): 1122–25, 1981). The isocyanates are converted to the N-methyl-1-naphthalenemethylamine (MNMA) urea derivatives.

The foregoing methods are incapable of correctly identifying or accurately quantifying all isocyanate species that may be present in a sample. Thus, there is a need for a simple method for detecting total isocyanate in an environmental sample, such as a solid, liquid, or air sample or a surface wipe sample.

SUMMARY OF THE INVENTION

A novel isocyanate derivitizing agent, useful for the determination of isocyanates in a sample, such as an environmental sample, is provided. The agent is 9-anthracenylmethyl-1-piperazinecarboxylate, referred to herein as "PAC." A method for producing PAC and a method for measuring the total level of isocyanate in an environmental sample are also provided.

PAC has the following chemical structure:

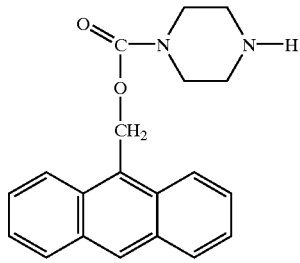

(I)

PAC is produced by adding 9-anthacenemethanol and pyridine to a solution of p-nitrophenyl chloroformate. Product is isolated to provide a crude anthrylmethyl p-nitrophenyl carbonate, which is then added to a solution of piperazine. The reacted mixture is poured into water and extracted with a solvent, preferably an organic solvent such as toluene. The product is washed and dried to provide 9-anthracenylmethyl-1-piperazinecarboxylate (PAC).

In accordance with the isocyanate detection method, a derivatizing agent such as PAC or a similar compound is used in conjunction with any conventional type of environmental sampling device, such as an air sampling device, to detect the total amount of isocyanate present in the sample. The air sample containing the isocyanate is collected by passing air through an impinger or bubbler containing a solution of a derivatizing agent, such as PAC, or through a filter or sorbent cartridge impregnated with a derivatizing agent. After the derivatizing agent binds with the isocyanate compound, a portion of the derivatizing agent molecule is cleaved from the derivatizing agent-isocyanate derivative and the cleaved portion is detected. The cleavage reaction is performed in a manner similar to the amine deprotection reactions described in Kornblum, et al. (*J. Org. Chem.*, 42(2): 399–400, 1977), which is incorporated by reference herein.

This method provides a distinct advantage over the isocyanate detection methods currently used by those skilled in the art because all of the isocyanate derivatives yield the same molecular cleavage residue, and total isocyanate levels are measured by simply measuring the amount of cleavage residue produced. Alternatively, if measurement of individual isocyanate species is desired, the individual species can be measured after derivatization but prior to cleavage.

This method also provides an advantage over the prior art by allowing for the detection of isocyanate groups chemically bound to solid or particle surfaces, such as wood composites or polyurethane.

Accordingly, it is an object of the present invention to provide an isocyanate derivatizing agent that is capable of derivatizing all isocyanate species.

It is another object of the present invention to provide an efficient method for producing the isocyanate derivatizing agent 9-anthracenylmethyl-1-piperazinecarboxylate.

It is yet another object of the present invention to provide a rapid, sensitive, inexpensive and efficient method for the detection and quantification of isocyanates in a sample.

It is a further object of the present invention to provide an effective method for the detection of isocyanates bound to solid or particle surfaces.

BRIEF DESCRIPTION OF THE DRAWINGS

FIG. 2 depicts the elution of the isocyanate monomers HDI-PAC, TDI-PAC, and MDI-PAC, as well as the PAC cleavage residue (designated as AMMS) using HPLC.

DETAILED DESCRIPTION OF THE PREFERRED EMBODIMENTS

Figure 1:
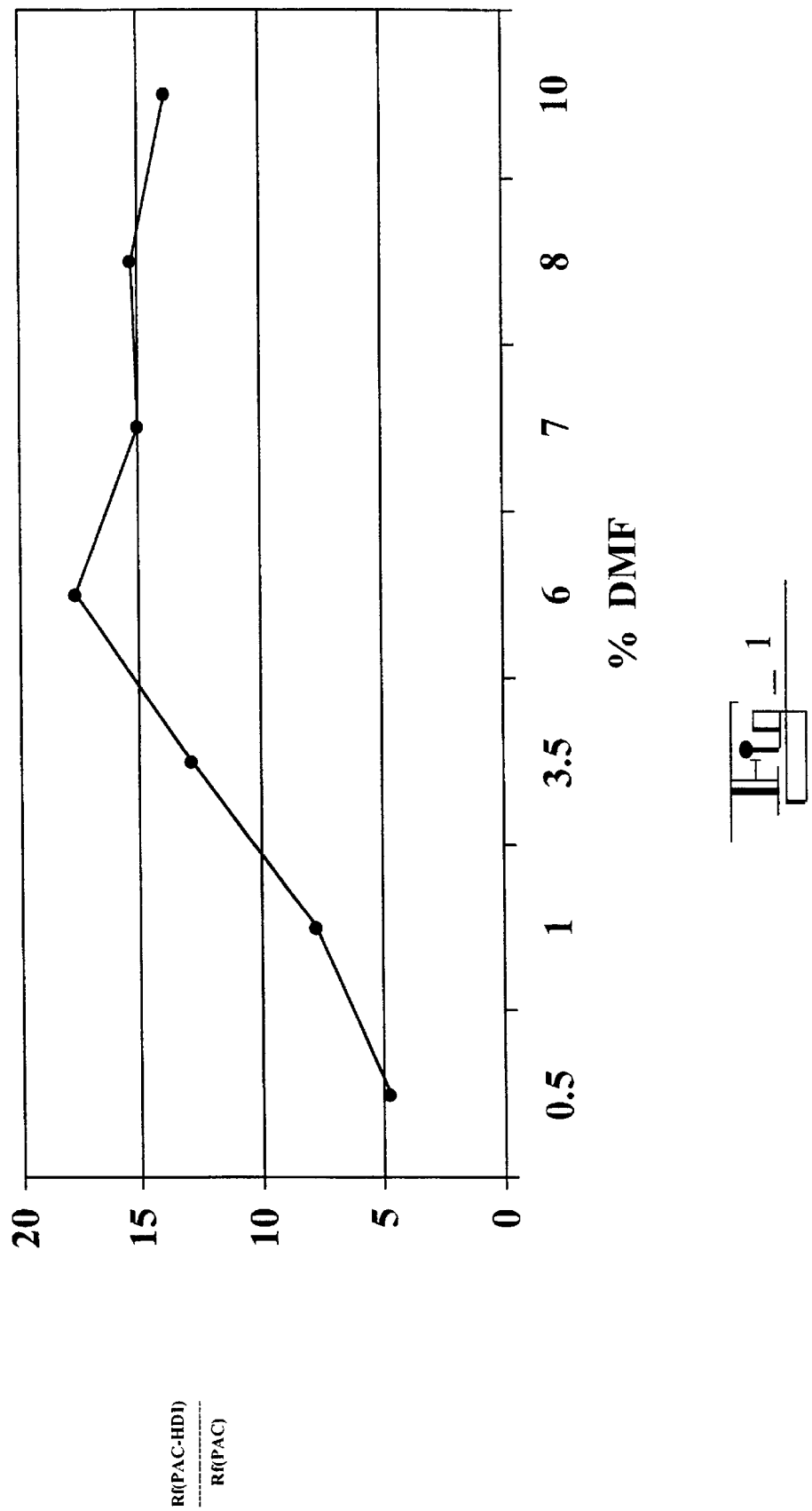
FIG. 1 shows the efficiency of chromatographic separation of PAC and HDI-PAC as a function of the percentage of dimethylformamide (DMF) in acetonitrile.

A novel organic compound, useful as an isocyanate derivatizing agent, is provided. The compound is 9-anthracenylmethyl-1-piperazinecarboxylate (PAC). Methods of producing PAC and methods of detecting and measuring isocyanate contaminant concentrations in an environmental sample using a derivatizing agent such as PAC are also provided.

While other known isocyanate detection methods require separate measurement of each isocyanate species, the method described herein advantageously allows for detection of all isocyanate groups in a single measurement. In accordance with the isocyanate detection method, the isocyanate derivatizing agent first binds to the isocyanate species at the isocyanate functional group, —N=C=O. Then. a portion of the derivatizing agent molecule is cleaved from the derivatized isocyanate to provide a cleavage residue. This cleavage residue is the same, regardless of the particular isocyanate species present. Thus, the quantity of cleavage product is equal to the total quantity of isocyanate present in the sample.

Derivatizin Agent and Method of Production

PAC has the following chemical structure:

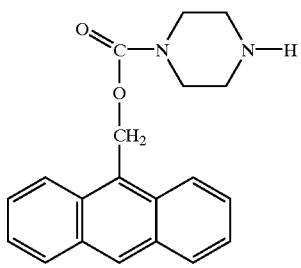

(I)

PAC can be synthesized by the following organic synthesis process. First, 9-anthacenemethanol and pyridine are added to a solution of p-nitrophenyl chloroformate. The reaction is monitored with thin-layer chromatography (TLC). Once complete, product is isolated to provide a crude anthrylmethyl p-nitrophenyl carbonate, which is then added to a solution of piperazine. The reaction between the crude anthrylmethyl p-nitrophenyl carbonate and piperazine is also monitored with TLC. Once complete, the reaction mixture is poured into water and extracted with a solvent, preferably an organic solvent such as toluene. The product is washed and dried to provide 9-anthracenylmethyl-1-piperazinecarboxylate (PAC). The product is then purified, for example, by recrystallization and/or silica gel chromatography.

Isocyanate Detection Method

Isocyanates in a sample can be detected and quantified by the following method. This method can be used to quantify individual isocyanate monomers or to identify the total amount of isocyanate present in a sample, regardless of the individual isocyanate species present.

A sample, such as an environmental sample, is obtained using conventional sampling techniques known to those skilled in the art. The sample can be any environmental sample containing or suspected of containing isocyanates. Exemplary environmental samples include, but are not limited to, solids, liquids, air, and surface swipe samples. Preferably, the environmental sample is an air sample, most preferably an air sample from a manufacturing facility that employs isocyanates. The sample may be obtained by any method, for example, by taking discreet samples at periodic intervals.

An air sample containing a concentration of isocyanate to be detected or measured is contacted with a suitable medium, such as an aprotic organic solvent, containing the derivatizing agent of the present invention. Typically, impingers or bubblers containing the solution of derivatizing agent, filters coated with the derivatizing agent, or sorbents coated with the derivatizing agent are used to contact the sample and the derivatizing agent. Preferably, the sample is collected by passing air through an impinger or bubbler containing a solution of a derivatizing agent, such as PAC, or through a filter or sorbent cartridge impregnated with the derivatizing agent.

The present method can be used to detect the total amount of isocyanate in a sample or to detect individual isocyanate derivatives. When the present method is used to detect total isocyanate, it is necessary to remove excess derivatizing agent because its presence can give an inaccurately high value. Once excess derivatizing agent has been removed, a portion of the derivatizing agent molecule is cleaved from the derivatizing agent-isocyanate derivative, followed by detection of the cleavage residue. When detection of only individual isocyanate derivatives is desired, the entire derivatizing agent-isocyanate derivative may be detected without the necessity of cleaving the derivatizing agent-isocyanate derivative and without prior removal of excess derivatizing agent.

Filters useful in the present invention are generally 13 mm, 25 mm, or 37 mm in diameter. The filter matrix into which the derivatizing agent is impregnated is preferably glass fiber or quartz fiber. Air is generally drawn through the filter with personal sampling pumps, typically at a rate of about 1 to 2 liters per minute.

The isocyanate-derivatizing agent with which the filter matrix is coated is a compound having the chemical formula of formula II, below:

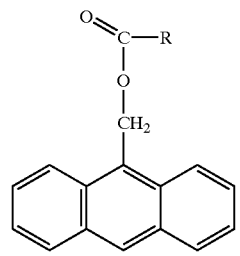

(II)

wherein R is a radical having a single isocyanate-derivatizing functionality comprising a primary or secondary amine.

The chemical reactions which take place in the derivatization and cleavage can be depicted by the following reaction scheme using PAC as the derivatizing agent:

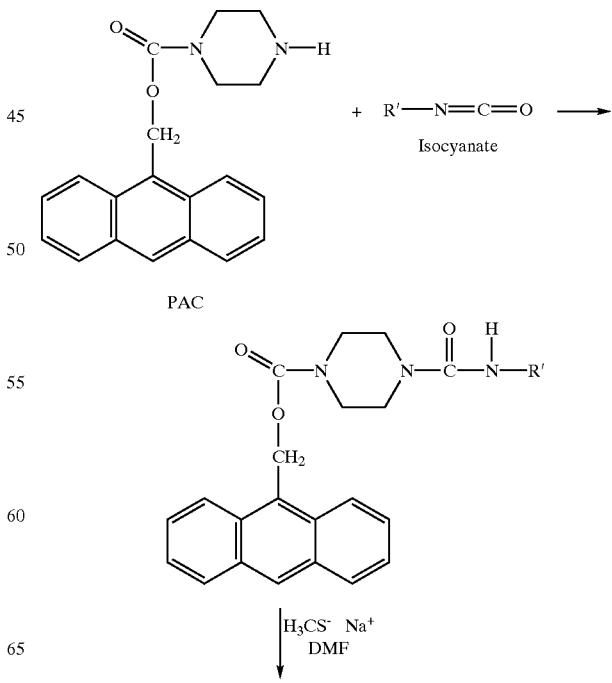

-continued

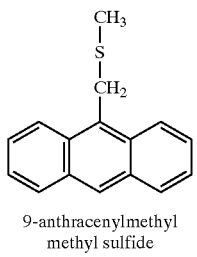 + 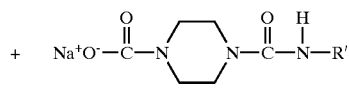

9-anthracenylmethyl methyl sulfide

The derivatizing reagent reacts with the isocyanate functional groups of any isocyanate species present in the sample to form derivatized isocyanates which are a mixture of intermediate ureas.

The mixture of intermediate ureas is then separated from excess PAC in the reaction mixture. Separation of excess derivatizing reagent is preferably achieved by passing the reaction mixture through a solid-phase extraction cartridge, such as a silica gel column, which retains both the mixture of intermediate ureas and any unreacted derivatizing agent. Separation of excess derivatizing reagent is important when using the present method to detect the total amount of isocyanate in the sample because the excess derivatizing agent will react with the cleavage agent to produce excess cleavage product. The mixture of intermediate ureas is then eluted from the column with an appropriate solvent, such as dimethylformamide (DMF). The DMF is generally used in concentrations from 1% to 10% in an appropriate solvent, such as acetonitrile, with 6% DMF being preferred.

In one preferred embodiment, a sample of the mixture of intermediate ureas is analyzed using, for example, high performance liquid chromatography (HPLC) to determine the quantity of one or more specific isocyanate species in the sample. Thus, the present invention can be used to determine the quantity of individual isocyanate species within a given air sample (see FIG. 2).

In a second preferred embodiment, the mixture of intermediate ureas is reacted with a cleaving agent, such as sodium thiomethoxide or trifluoroacetic acid, to form a cleavage product, such as 9-anthracenylmethyl methyl sulfide. The cleavage product can then be quantified, for example, by high performance liquid chromatography (HPLC) equipped with an appropriate detector, such as a fluorescence detector. The concentration of cleavage product is equal to the total concentration of isocyanate present in the air sample (see FIG. 2).

In a third preferred embodiment, PAC or a derivatizing agent of formula II, as provided above, is used to detect isocyanate compounds bound to a solid or particle surface. The solid surface or particles are treated with the derivatizing agent which reacts with the free isocyanate groups on the surface. Excess derivatizing agent is then removed from the surface by solvent extraction. The solid surface or particles are then treated with sodium thiomethoxide solution to generate 9-anthracenylmethyl methyl sulfide from the chemically bound isocyanate groups.

The preferred isocyanate-derivatizing agent to be used in the method is PAC, which is prepared as described above. Isocyanate-derivatizing agents other than PAC, which are useful for detecting or measuring isocyanates in a sample, are described in more detail below. These isocyanate-derivatizing agents can be produced by a process similar to the PAC production process by first producing the crude anthrylmethyl p-nitrophenyl carbonate intermediate as described above, followed by reaction of the particular amine with the intermediate.

While PAC is the preferred compound, other anthrylmethyl compounds are also useful in the method of the present invention. Such compounds include, but are not limited to, those having the following formula:

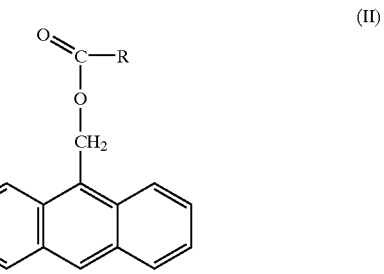

(II)

wherein R is a radical having a single isocyanate-derivatizing functionality comprising a primary or secondary amine. Preferred compounds of the present invention are those in which R comprises a radical of a primary or secondary diamine. Especially preferred compounds are those in which R comprises a radical of an aliphatic primary or secondary diamine. The most preferred compounds of the present invention are those in which R comprises a radical of a symmetrical aliphatic primary or secondary diamine. Examples of contemplated R groups include, but are not limited to, substituted or unsubstituted radicals of piperidine, piperazine, 1,2-diaminoethane, 1,3-diaminopropane, 1,4-diaminobutane, 1,5-diaminopentane, 1,6-diaminopropane, and 4,4'-bipiperidine.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Preparation of Anthrylmethyl p-Nitrophenyl Carbonate 4.89 g (24 mmoles) of p-nitrophenyl chloroformate were dissolved in 100 ml of tetrahydrofuran (THF) and placed in a two-neck, 500 ml round bottom flask with a magnetic stirring bar.

3.36 g (16.2 mmoles) of 9-anthacenemethanol were dissolved in 100 ml of THF, and 2.56 g (2.61 ml, 32.4 mmoles) of pyridine were added to the anthracenemethanol solution. The anthracenemethanol. solution was then added dropwise to the p-nitrophenyl chloroformate solution, while monitoring the progress of the reaction with thin-layer chromatography (TLC). The reaction mixture, a 3:2 ratio of p-nitrophenyl chloroformate: anthracenemethanol, was allowed to stir overnight.

The reaction mixture was then decanted to separate the solution from the white precipitate which had formed, followed by roto-evaporation to remove the THF. The product residue was dissolved in toluene. This solution was then decanted to remove any undissolved product residue.

Next, the toluene solution was roto-evaporated, yielding 8.60 g of crude anthrylmethyl p-nitrophenyl carbonate. This crude product also contained a small amount of unreacted p-nitrophenyl chloroformate.

EXAMPLE 2

Preparation of 9-Anthracenylmethyl-1-piperazinecarboxylate (PAC)

The crude anthrylmethyl p-nitrophenyl carbonate (8.60 g) produced in Example 1 was dissolved in 40 ml of dimethylformamide (DMF), and 14.0 g of piperazine (162 mmoles, 10 fold excess) were dissolved in 20 ml of DMF. The solution of crude anthrylmethyl p-nitrophenyl carbonate was then added dropwise to the piperazine solution while stirring constantly. The reaction was monitored with TLC.

After 45 minutes, the reaction mixture was poured into 100 ml of ice water and extracted with toluene. The toluene extract was washed once with 100 ml of a 10% sodium carbonate solution and twice with 100 ml of deionized water. The toluene extract was then passed through a sodium sulfate column to remove any residual water, followed by roto-evaporatation to produce 9-anthracenylmethyl-1-piperazinecarboxylate (PAC).

Two recrystallizations of the product PAC were performed in a solvent system of toluene and hexane, yielding 3.09 g PAC (59.5% yield) in a non-optimized procedure. 1.49 g of the recrystallized PAC were dissolved in 22 ml of toluene, layered on a 500 ml silica gel column, and eluted with methanol. Twelve 250 ml fractions were collected with fractions 7–10 containing the PAC. These fractions were roto-evaporated, yielding 1.35 g PAC.

EXAMPLE 3

Preparation of the Urea of Phenyl Isocyanate and PAC 0.63 g (1.96 mmoles) of PAC were dissolved in 35 ml of toluene, and 0.26 g (2.2 mmoles, 10% excess) of phenyl isocyanate were dissolved in 10 ml of toluene. The phenyl isocyanate solution was added dropwise to the PAC solution, while stirring constantly. A precipitate formed shortly after the initial addition of phenyl isocyanate. The reaction mixture was allowed to stir for an additional 20 minutes after the final addition of phenyl isocyanate.

The precipitate was separated by filtration through a fritted glass funnel. The precipitate was washed three times with small amounts of toluene and twice with hexane. The precipitate, the urea of phenyl isocyanate and PAC, weighed 0.81 g (94% yield).

EXAMPLE 4

Cleavage of Phenyl-isocyanate-PAC Urea with Sodium Thiomethoxide

Using solvent purged with nitrogen, 404 mg (0.91 mmoles) of the urea of phenyl isocyanate and PAC were dissolved in 40 ml of DMF. 474 mg (6.76 mmoles) of sodium thiomethoxide were dissolved in 40 ml of DMF. The solution of the urea was added to the sodium thiomethoxide solution while stirring constantly and purging the atmosphere above the reaction with nitrogen. The reaction was monitored with TLC.

After 60 minutes, 160 ml of ice cold 1 M HCl was added to the reaction mixture. The aqueous acidic phase was extracted with 80 ml of toluene, followed by a second extraction with 40 ml of toluene. Most of the product was recovered in the first extract as monitored by TLC. Both extracts were washed first with 1 M HCl and then with deionized water.

The washed toluene extracts were then roto-evaporated to dryness. The crude product was dissolved in 10 ml of toluene and loaded onto a 100 ml silica gel column. The column was eluted with about 600 ml of hexane to remove impurities, followed by 2:1 hexane:ethyl acetate solution which quickly eluted the desired product. The fractions containing the product were then roto-evaporated, yielding 193 mg (88% yield) 9-anthracenylmethyl methyl sulfide.

The sodium thiomethoxide solution used in this experiment is very sensitive to oxidation by air. If the sodium thiomethoxide solution is prepared under nitrogen but stored in air, it is only usable for one day. However, if the solution is both prepared and stored in nitrogen, it is stable for about one week. Concentrated solutions of the sodium thiomethoxide reagent prepared in methanol (100 mg/ml) can be stored for one week and then diluted with DMF for use in the reaction as described in this experiment.

EXAMPLE 5

Comparison of Elution of PAC-Ureas and PAC by TLC Using 5% DMF in Acetonitrile as the Elution Solvent It is important to remove excess PAC from the PAC-isocyanate ureas prior to the cleavage reaction because the cleavage agent will also result in cleavage of unreacted PAC to give an inaccurate measurement of isocyanate levels. PAC can be readily separated from the urea mixture as shown in this example. In practice, this separation would be performed through solid-phase extraction.

PAC and the PAC isocyanate ureas listed below in Table 1 were individually dissolved in DMF at concentrations of approximately 0.1–0.5%. One microliter of each sample solution was then placed 15 mm from the bottom of a 90 mm silica gel TLC plate. Next, the DMF spotting solvent was removed by subjecting the plate to a high vacuum. The plate was then placed in the developing chamber in 10 ml of 5% DMF in acetonitrile and the solvent was allowed to climb the plate until 60 mm above the original spotting position. At this point the plate was removed from the developing chamber, the solvent was allowed to evaporate, and the position of the spots was evaluated under a UV light. The distance between the center of the spot and the original position of the spot was used as the migration distance. $R_f$, which is a measure of the extent of movement of a compound along the plate, was calculated as the ratio of the migration distance to the total distance traveled by the solvent. Then, the $R_f$ for the PAC-urea was divided by the $R_f$ for PAC to give a measure of the degree of separation of the two compounds.

TABLE 1

| Compound | Mobile Phase | Migration (mm) | Length (mm) | Rf | $Rf_{urea}/Rf_{PAC}$ |
|---|---|---|---|---|---|
| PAC | 5.0% DMF | 1.8 | 60 | 0.030 | |
| PAC-phenyl | 5.0% DMF | 55.5 | 60 | 0.925 | 30.8 |
| PAC-butyl | 5.0% DMF | 50.2 | 60 | 0.837 | 27.9 |
| PAC #2 | 5.0% DMF | 1.8 | 60 | 0.030 | |
| PAC-MDI | 5.0% DMF | 49.2 | 60 | 0.820 | 27.3 |
| PAC-TDI | 5.0% DMF | 43.1 | 60 | 0.718 | 23.9 |
| PAC #3 | 5.0% DMF | 1.7 | 60 | 0.028 | |
| PAC-HDI | 5.0% DMF | 27.9 | 60 | 0.465 | 16.6 |

EXAMPLE 6

Comparison of Elution of PAC and PAC-HDI Urea as a Function of %DMF in Acetonitrile The procedure provided in Example 5 was repeated using PAC and PAC-HDI (PAC-hexamethylene diisocyanate urea). The percentage of DMF in the acetonitrile was varied to determine the optimum DMF concentration for separation of unreacted PAC from the PAC-isocyanate ureas. As seen in Table 2 below and in FIG. 1, 6% DMF in acetonitrile was found to be the optimum elution solvent for separating excess PAC from the PAC-isocyanate ureas.

TABLE 2

| Compound | Mobile Phase | Migration (mm) | Length (mm) | Rf | $Rf_{HDI}/Rf_{PAC}$ |
|---|---|---|---|---|---|
| PAC | 0% DMF | 0.8 | 60 | 0.013 | |
| PAC-HDI | 0% DMF | 1.6 | 60 | 0.027 | 2.0 |
| PAC | 0.5% DMF | 0.7 | 60 | 0.012 | |
| PAC-HDI | 0.5% DMF | 3.3 | 60 | 0.055 | 4.7 |
| PAC | 1.0% DMF | 0.7 | 60 | 0.012 | |
| PAC-HDI | 1.0% DMF | 5.4 | 60 | 0.090 | 7.7 |
| PAC | 2.0% DMF | 1.0 | 60 | 0.017 | |
| PAC-HDI | 2.0% DMF | 10.8 | 60 | 0.180 | 10.8 |
| PAC | 2.0% DMF | 1.4 | 70 | 0.020 | |
| PAC-HDI | 2.0% DMF | 13.3 | 70 | 0.190 | 9.5 |
| PAC | 2.0% DMF | 1.3 | 60 | 0.022 | |
| PAC-HDI | 2.0% DMF | 11.2 | 60 | 0.187 | 8.6 |
| PAC | 3.5% DMF | 1.6 | 60 | 0.027 | |
| PAC-HDI | 3.5% DMF | 20.4 | 60 | 0.340 | 12.8 |
| PAC | 5.0% DMF | 1.7 | 60 | 0.028 | |
| PAC-HDI | 5.0% DMF | 27.9 | 60 | 0.465 | 16.6 |
| PAC | 6.0% DMF | 2.0 | 60 | 0.033 | |
| PAC-HDI | 6.0% DMF | 35.4 | 60 | 0.590 | 17.7 |
| PAC | 7.0% DMF | 2.4 | 60 | 0.040 | |
| PAC-HDI | 7.0% DMF | 35.9 | 60 | 0.600 | 15.0 |
| PAC | 7.5% DMF | 2.5 | 60 | 0.042 | |
| PAC-HDI | 7.5% DMF | 42.5 | 60 | 0.708 | 17.0 |
| PAC | 8.0% DMF | 2.6 | 60 | 0.043 | |
| PAC-HDI | 8.0% DMF | 39.8 | 60 | 0.663 | 15.3 |
| PAC | 10% DMF | 3.2 | 60 | 0.053 | |
| PAC-HDI | 10% DMF | 44.0 | 60 | 0.733 | 13.8 |

MAP, 1-(9-anthracenylmethyl)piperazine, is an isocyanate derivatizing agent having a structure similar to PAC:

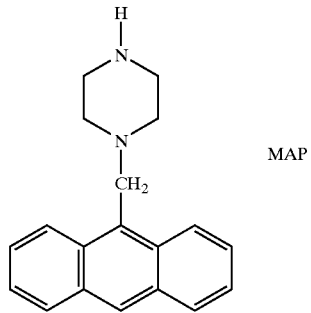

MAP

The use of MAP for the detection of isocyanates is the subject matter of U.S. Pat. No. 5,354,689. The advantage of PAC over MAP is its ability to detect all species of isocyanates through the PAC cleavage residue. MAP is not able to form such a residue and, therefore, only measures individual species of isocyanates.

EXAMPLE 7

PAC versus MAP Kinetic Study

Because isocyanates are highly reactive and exist in samples together with compounds that can react with them (e.g., polyols and water), derivatizing reagents must react with isocyanates sufficiently fast to avoid losses to these side reactions. Also, efficient collection of isocyanate vapors on a reagent-impregnated filter requires rapid derivatization. In this experiment, phenyl isocyanate was reacted with an equimolar mixture of PAC and MAP, with the PAC and MAP to assess PAC's reactivity with isocyanates.

Aliquots of phenyl isocyanate were added to equimolar mixtures of MAP and PAC in acetonitrile at ½, ¼, and ⅛ the concentrations of the reagents and the samples were allowed to react overnight. The following day, acetic anhydride was added to the samples to react with the remaining reagents.

Standards were run for both MAP-phenyl urea and PAC-phenyl urea to generate a calibration curve with least squares fit. The standards ranged in concentration from the highest amount of the product that could be generated in an experiment down to 1/16 of that level. These calibration curves were then used to determine the quantity of each derivative in the samples. These quantities were then entered into the following equations to determine the ratio of rate constants for MAP and PAC:

Calibration equations:

PAC-phenyl urea: X=Y/1214.128

MAP-phenyl urea: X=Y/1148.733 where Y=peak area and X=mmole injected. Next, the ratio of the rate constants for MAP to PAC were determined by the following formula:

$$k_{MAP}/k_{PAC}=K.$$

Peak Areas

| Description | Acetylated PAC | Acetylated MAP | PAC phenyl urea | MAP phenyl urea |
|---|---|---|---|---|
| Low standard #1 | | | 68,028 | 62,979 |
| Low standard #2 | | | 61,507 | 58,216 |
| AVG. ± % DEV. | | | 64,768 ± 5.0% | 60,598 ± 3.9% |
| Medium Standard #1 | | | 251,176 | 235,661 |
| Medium Standard #2 | | | 246,968 | 232,855 |
| AVG. ± % DEV. | | | 249,072 ± 0.8% | 234,258 ± 0.6% |
| High Standard #1 | | | 1,077,690 | 1,000,289 |
| High Standard #2 | | | 999,382 | 925,234 |
| AVG. ± % DEV. | | | 1,038,536 ± 3.8% | 962,762 ± 3.9% |
| Low Sample #1 | 1,699,794 | 1,555,243 | 20,670 | 214,396 |
| Low Sample #2 | 1,734,055 | 1,596,514 | 18,659 | 218,618 |
| AVG. ± % DEV. | 1,716,925 ± 1.0% | 1,575,879 ± 1.3% | 19,665 ± 5.1% | 216,507 ± 1.0% |
| Medium Sample #1 | 1,714,101 | 1,392,583 | 42,219 | 431,589 |
| Medium Sample #2 | 1,675,666 | 1,368,163 | 37,611 | 419,244 |
| AVG. ± % DEV. | 1,694,884 ± 1.1% | 1,380,373 ± 0.9% | 39,915 ± 5.8% | 425,417 ± 1.5% |
| High Sample #1 | 1,624,022 | 988,570 | 89,799 | 826,717 |

-continued

| Description | Acetylated PAC | Acetylated MAP | PAC phenyl urea | MAP phenyl urea |
|---|---|---|---|---|
| High Sample #2 | 1,629,181 | 1,000,314 | 86,521 | 827,103 |
| AVG. ± % DEV. | 1,626,602 ± 0.2% | 994,442 ± 0.6% | 88,160 ± 1.9% | 826,910 ± 0.0% |

| Sample | PAC/phenyl Y | PAC/phenyl X | MAP/phenyl Y | MAP/phenyl X |
|---|---|---|---|---|
| Low | 19,665 | 16.20 | 216,507 | 188.44 |
| Medium | 39,915 | 32.88 | 425,417 | 370.27 |
| High | 88,160 | 72.61 | 826,910 | 719.72 |

X values are in terms of pmoles per injection = pmole/10 µl $$K = \frac{kMAP}{kPAC} = \frac{\log[(a-x)/a]}{\log[(b-y)/b]}$$

where
a = initial conc of MAP
b = initial conc of PAC
x = conc of MAP phenyl urea
y = conc of PAC phenyl urea
then

| Phenyl-isocyanate conc description | a | b | x | y | log[(a−x)/a] | log[(b−y)/b] | K |
|---|---|---|---|---|---|---|---|
| Low | 1680 | 1673.3 | 188.44 | 16.20 | −0.05167 | −0.00423 | 12.2 |
| Medium | 1680 | 1673.3 | 370.27 | 32.88 | −0.10813 | −0.00862 | 12.5 |
| High | 1680 | 1673.3 | 719.72 | 72.61 | −0.24291 | −0.01927 | 12.6 |

Yield of Products

| Sample | Phenyl-isocyanate (pm/10 µL) | PAC phenylurea (pm/10 µL) | MAP phenylurea (pm/10 µL) | Total Recovered | % Yield |
|---|---|---|---|---|---|
| Low | 208.33 | 16.20 | 188.44 | 204.64 | 98.2% |
| Medium | 416.67 | 32.88 | 370.27 | 403.15 | 96.8% |
| High | 833.33 | 72.61 | 719.72 | 792.33 | 95.1% |

The above examples are intended to be demonstrative, rather than limiting, of the embodiments contemplated by the invention and encompassed within the scope of the claims.

By measuring the relative amounts of PAC-phenyl urea and MAP-phenyl urea that were formed, the relative reaction rates of the two derivatizing agents were determined. The experimental results at all three levels of phenyl isocyanate were in agreement and almost all of the phenyl isocyanate was accounted for as either the PAC or MAP derivative. The results indicate that PAC reacts about 12–13 times more slowly with phenyl isocyanate than MAP does. Although PAC's reactivity with phenyl isocyanate is less than the MAP reagent, it is greater than the reactivity of at least one commonly used reagent, [N-(4-nitrobenzyl)propylamine], and considerably greater than that of the polyols and water against which it is competing for isocyanate.

I claim:

1. A compound having the following formula:

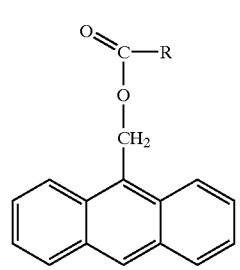

(II)

wherein R comprises a radical having a single isocyanate-derivatizing functionality comprising a primary or secondary amine.

2. The compound of claim 1 wherein R comprises a radical of a symmetrical aliphatic primary or secondary diamine.

3. The compound of claim 1 wherein R is selected from the group consisting of a substituted or unsubstituted radical of piperazine, piperidine, 4,4'- bipiperidine, 1,2-diaminoethane, 1,3-diaminopropane, 1,4-diaminobutane, 1,5-diaminopentane, and 1,6-diaminiohexane.

4. The compound of claim 3 having the formula:

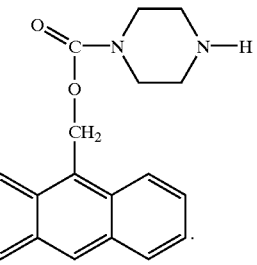

5. A process for preparing 9-anthracenylmethyl-1-piperazinecarboxylate (PAC) comprising:
   (a) reacting 9-anthracenemethanol, pyridine, and p-nitrophenyl chloroformate to produce anthrylmethyl p-nitrophenyl carbonate;

(b) isolating the anthrylmethyl p-nitrophenyl carbonate produced in step (a); and (c) reacting the anthrylmethyl p-nitrophenyl carbonate isolated in step (b) with piperazine to produce 9-anthracenylmethyl-1-piperazine-carboxylate.

6. A method for determining the total amount of isocyanate in a sample comprising:

(a) contacting the sample with an isocyanate-derivatizing agent having the following formula:

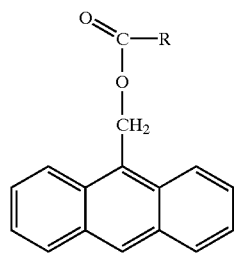

(II)

wherein R comprises a radical of a primary or secondary amine to form a mixture of ureas;

(b) separating the mixture of ureas from unreacted derivatizing agent;

(c) reacting the ureas with sodium thiomethoxide to form 9-anthracenylmethyl methyl sulfide; and (d) quantifying the amount of 9-anthracenylmethyl methyl sulfide produced.

7. The method of claim 6 wherein R comprises a radical of a symmetrical aliphatic primary or secondary diamine.

8. The method of claim 6 wherein R is selected from the group consisting of a substituted or un substituted radical of piperazine, piperidine, 4,4'-bipiperidine, 1,2-diaminoethane, 1,3-diaminopropane, 1,4-diaminobutane, 1,5-diaminopentane, and 1,6-diaminohexane.

9. The method of claim 8 wherein the isocyanate-derivatizing agent is a compound having the following formula:

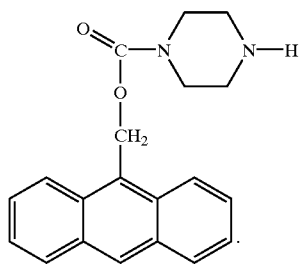

10. The method of claim 6 wherein the 9-anthracenylmethyl methyl sulfide is quantified using chromatographic methods.

11. The method of claim 10 wherein the 9-anthracenylmethyl methyl sulfide is quantified using high performance liquid chromatography (HPLC) equipped with a fluorescence detector.

12. A method for determining the amount of individual isocyanates in a sample comprising:

(a) contacting the sample with an isocyanate-derivatizing agent having the following formula:

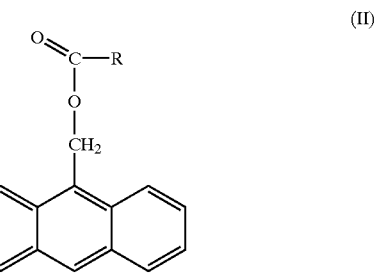

(II)

wherein R comprises a radical of a primary or secondary amine to form a mixture of ureas;

(b) detecting individual ureas within the sample;

(c) quantifying the amount of urea, wherein the amount of urea corresponds to the individual isocyanate being determined.

13. The method of claim 12 wherein R comprises a radical of a symmetrical aliphatic primary or secondary diamine.

14. The method of claim 12 wherein R is selected from the group consisting of a substituted or unsubstituted radical of piperazine, piperidine, 4,4'-bipiperidinie, 1,2-diaminoethane, 1,3-diaminopropane, 1,4-diaminobutane, 1,5-diaminopentane, and 1,6-diaminiohexane.

15. The method of claim 14 wherein the isocyanate-derivatizing agent is a compound having the following formula:

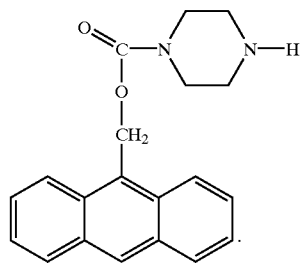

16. The method of claim 12 wherein the urea is quantified using chromatographic methods.

17. The method of claim 16 wherein the urea is quantified using high performance liquid chromatography (HPLC) equipped with a fluorescence detector.

18. A method for determining the total amount of isocyanate on a solid or particle surface comprising:

(a) contacting a solid or particle surface with an isocyanate-derivatizing agent having the following formula:

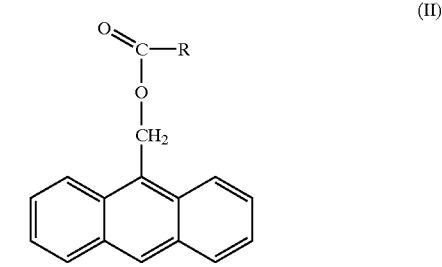

(II)

wherein R comprises a radical of a primary or secondary amine;

(b) treating the solid or particle surface with a solvent to extract excess isocyanate-derivatizing agent;

(c) treating the solid or particle surface with sodium thiomethoxide to form 9-anthracenylmethyl methyl sulfide; and (d) quantifying the amount of 9-anthracenylmethyl methyl sulfide produced.

19. The method of claim 18 wherein R comprises a radical of a symmetrical aliphatic primary or secondary diamine.

20. The method of claim 18 wherein R is selected from the group consisting of a Substituted or unsubstituted radical of piperazine, piperidine, 4,4'-bipiperidinie, 1,2-diaminoethane, 1,3-diaminopropane, 1,4-diaminobutane, 1,5-diaminopentane, and 1,6-diaminiohexane.

21. The method of claim 20 wherein the isocyanate-derivatizing agent is a compound having the following formula:

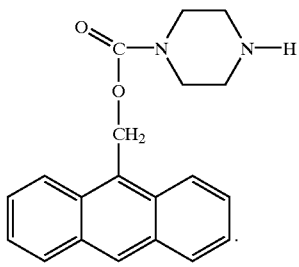

22. The method of claim 18 wherein the 9-anthracenylmethyl methyl sulfide is quantified using chromatographic methods.

23. The method of claim 22 wherein the 9-anthracenylmethyl methyl sulfide is quantified using high performance liquid chromatography (HPLC) equipped with a fluorescence detector.

24. The method of claim 18 wherein the solid or particle is selected from the group consisting of polyurethane and dust from wood composites.

* * * * *